US012714476B2

(12) United States Patent
Loutzenhiser et al.

(10) Patent No.: US 12,714,476 B2
(45) Date of Patent: Aug. 25, 2026

(54) GRAFT SCAFFOLD

(71) Applicant: K2M, Inc., Leesburg, VA (US)

(72) Inventors: Lonnie Loutzenhiser, Denver, CO (US); Joseph Michael Meyer, Bethel, OH (US); Daniel Tavani, Duluth, GA (US)

(73) Assignee: VB Spine US Opco LLC, Leesburg, VA (US)

( * ) Notice: Subject to any disclaimer, the term of this patent is extended or adjusted under 35 U.S.C. 154(b) by 1274 days.

(21) Appl. No.: 17/281,838

(22) PCT Filed: Oct. 1, 2019

(86) PCT No.: PCT/US2019/054030
§ 371 (c)(1),
(2) Date: Mar. 31, 2021

(87) PCT Pub. No.: WO2020/072469
PCT Pub. Date: Apr. 9, 2020

(65) Prior Publication Data

US 2022/0008104 A1 Jan. 13, 2022

Related U.S. Application Data

(60) Provisional application No. 62/739,453, filed on Oct. 1, 2018.

(51) Int. Cl.
*A61B 17/70* (2006.01)
*A61L 27/36* (2006.01)

(52) U.S. Cl.
CPC ........ *A61B 17/7065* (2013.01); *A61B 17/707* (2013.01); *A61L 27/3608* (2013.01); *A61L 27/365* (2013.01); *A61L 2430/38* (2013.01)

(58) Field of Classification Search
CPC ............ A61B 17/7044; A61B 17/7062; A61B 17/707; A61B 17/7065
See application file for complete search history.

(56) References Cited

U.S. PATENT DOCUMENTS 5,649,925 A * 7/1997 Barbera Alacreu .......................... A61B 17/7013 606/103
6,037,519 A * 3/2000 Mckay .................... A61L 27/54 524/415

(Continued)

FOREIGN PATENT DOCUMENTS

WO 9418910 A1 9/1994
WO 2007075375 A2 7/2007

(Continued)

OTHER PUBLICATIONS

International Search Report including Written Opinion for Application No. PCT/US2019/0540305, mailed Jan. 16, 2020, pp. 1-15.

(Continued)

*Primary Examiner* — Eduardo C Robert
*Assistant Examiner* — Michelle C Green
(74) *Attorney, Agent, or Firm* — Lerner David LLP

(57) ABSTRACT

An implant that can hold bone graft material, and receive support from adjacent tissues and structures. In one aspect, the implant has an attachment region to directly engage with adjacent tissues and structures. In another aspect, the implant is malleable and can be manipulated to conform to the adjacent tissues and structures.

19 Claims, 14 Drawing Sheets

(56) References Cited

U.S. PATENT DOCUMENTS

| | | | | |
|---|---|---|---|---|
| 6,060,641 | A | 5/2000 | Manolidis | |
| 6,719,795 | B1* | 4/2004 | Cornwall | A61B 17/707 606/264 |
| 7,537,664 | B2 | 5/2009 | O'Neill et al. | |
| 8,728,387 | B2 | 5/2014 | Jones et al. | |
| 9,135,374 | B2 | 9/2015 | Jones et al. | |
| 9,180,010 | B2 | 11/2015 | Dong et al. | |
| 9,439,685 | B2* | 9/2016 | Bullard | A61L 27/54 |
| 9,456,901 | B2 | 10/2016 | Jones et al. | |
| 9,592,083 | B2* | 3/2017 | Walsh | A61F 2/44 |
| 9,724,205 | B2* | 8/2017 | Lin | A61F 2/4455 |
| 9,987,051 | B2 | 6/2018 | Nunley et al. | |
| 10,028,841 | B2 | 7/2018 | Moore et al. | |
| 10,271,958 | B2 | 4/2019 | Schaufler et al. | |
| 10,398,559 | B2 | 9/2019 | Jones et al. | |
| 10,596,660 | B2 | 3/2020 | McCarthy et al. | |
| 10,660,763 | B2 | 5/2020 | Wilson et al. | |
| 10,849,764 | B2 | 12/2020 | Moore et al. | |
| 2002/0123750 | A1 | 9/2002 | Eisermann et al. | |
| 2004/0249464 | A1 | 12/2004 | Bindseil et al. | |
| 2004/0259972 | A1* | 12/2004 | Ringeisen | A61L 27/3804 523/113 |
| 2005/0131407 | A1* | 6/2005 | Sicvol | A61B 17/7013 606/279 |
| 2006/0004358 | A1* | 1/2006 | Serhan | A61B 17/70 606/92 |
| 2006/0064090 | A1* | 3/2006 | Park | A61B 17/7005 606/259 |
| 2006/0184246 | A1 | 8/2006 | Zwirkoski | |
| 2006/0233853 | A1* | 10/2006 | Remington | A61L 27/54 424/422 |
| 2007/0016204 | A1* | 1/2007 | Martinez | A61B 17/7059 606/279 |
| 2007/0156145 | A1* | 7/2007 | Demakas | A61B 17/7059 606/250 |
| 2007/0270844 | A1* | 11/2007 | Lin | A61F 2/4455 606/279 |
| 2009/0326589 | A1* | 12/2009 | Lemoine | A61B 17/7064 606/280 |
| 2010/0266660 | A1* | 10/2010 | McKay | A61P 43/00 623/23.51 |
| 2013/0103091 | A1* | 4/2013 | Acosta, Jr. | A61B 17/7013 606/264 |
| 2013/0144386 | A1* | 6/2013 | Horton | A61B 17/707 623/17.11 |
| 2014/0058511 | A1* | 2/2014 | Strippgen | A61B 17/7055 623/16.11 |
| 2014/0277462 | A1 | 9/2014 | Yerby et al. | |
| 2016/0213405 | A1 | 7/2016 | Moore et al. | |
| 2017/0014235 | A1 | 1/2017 | Jones et al. | |
| 2018/0333780 | A1 | 11/2018 | Klein et al. | |
| 2019/0328424 | A1* | 10/2019 | Suddaby | A61B 17/7011 |

FOREIGN PATENT DOCUMENTS

| | | | |
|---|---|---|---|
| WO | 2014145527 | A2 | 9/2014 |
| WO | 2015028853 | A1 | 3/2015 |

OTHER PUBLICATIONS

Lee et al., U.S. Appl. No. 62/517,456, filed Jun. 9, 2017, titled "Polymer Interlock Support Structure and Method of Manufacture Thereof".

Moore et al., U.S. Appl. No. 62/108,197, filed Jan. 27, 2015, titled "Spinal Implant".

Moore et al. U.S. Appl. No. 62/196,371, filed Jul. 24, 2015, titled "Spinal Implant".

Stamp et al., U.S. Appl. No. 62/520,221, filed Jun. 15, 2017, titled "Porous Structures Produced by Additive Layer Manufacturing".

* cited by examiner

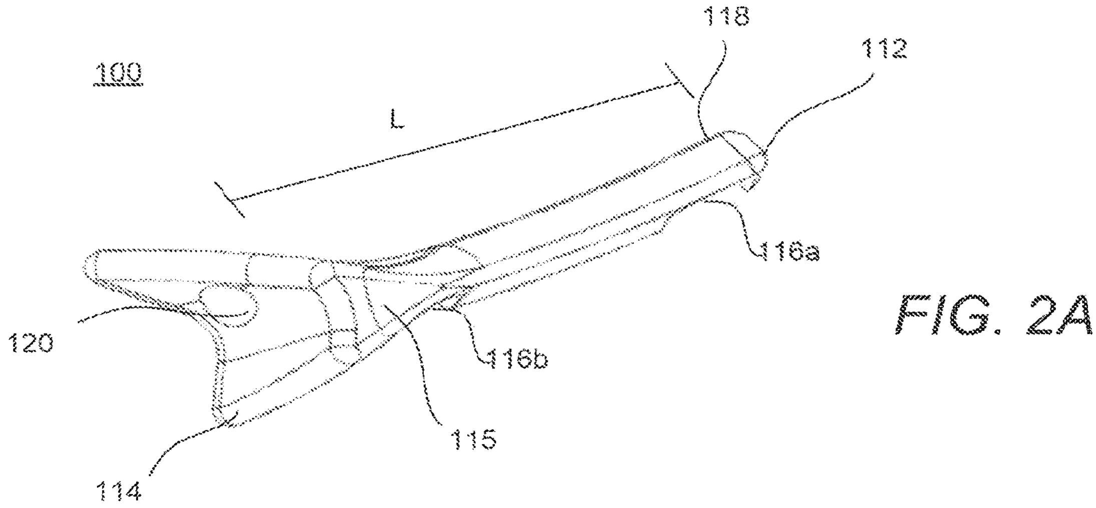
FIG. 2A
FIG. 2B
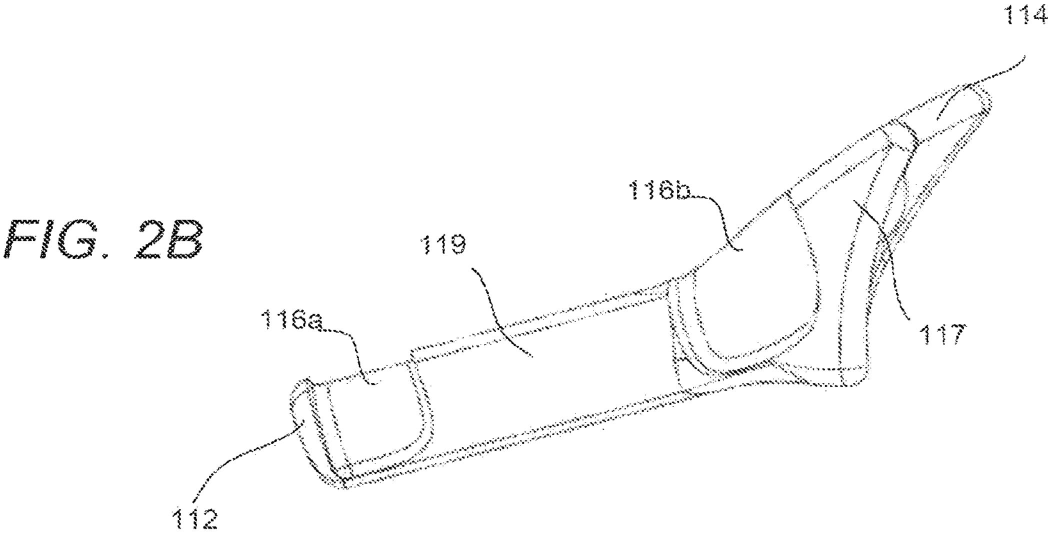
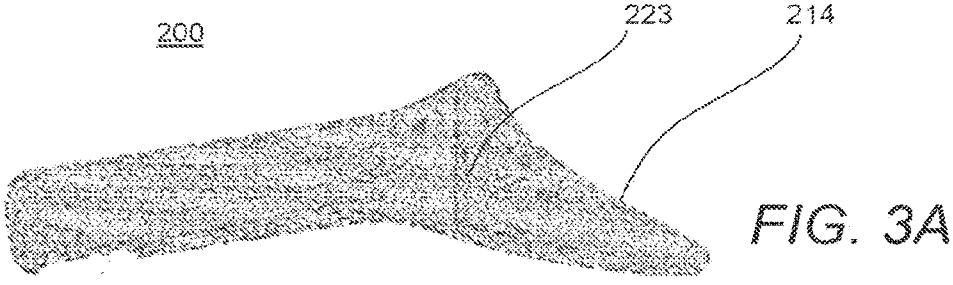
FIG. 3A

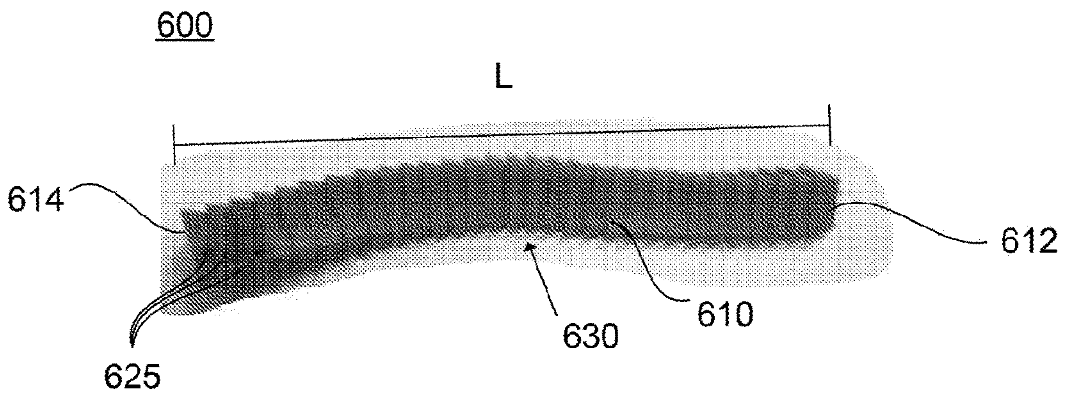
FIG. 7A
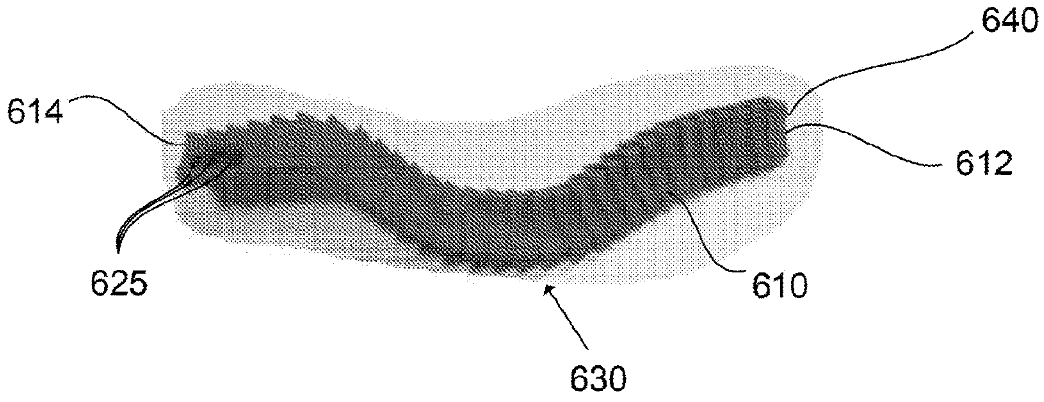
FIG. 7B
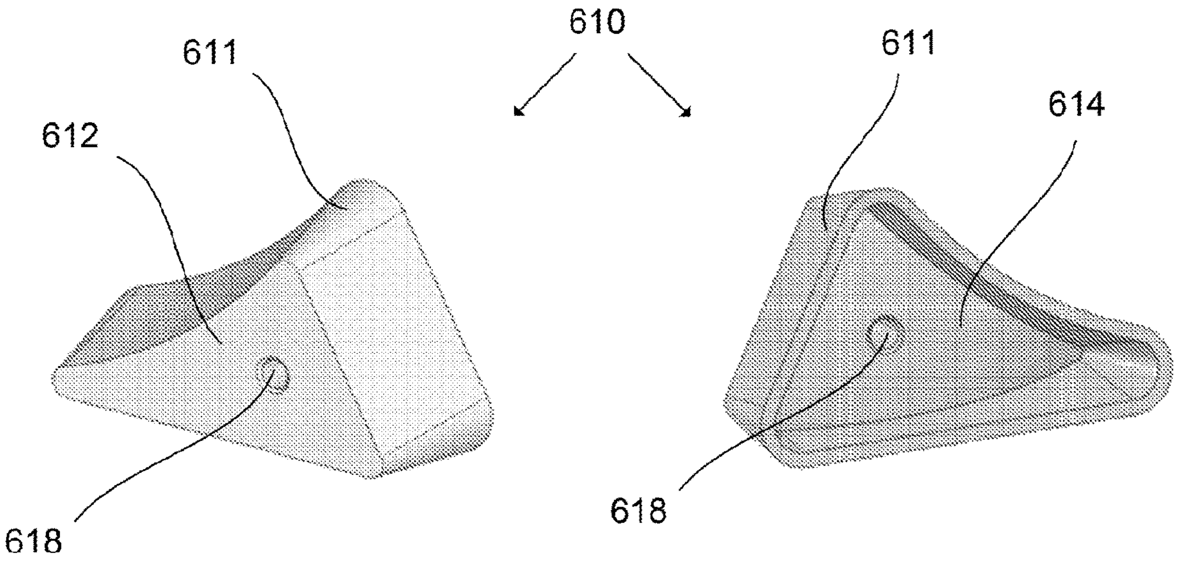
FIG. 7C
FIG. 7D

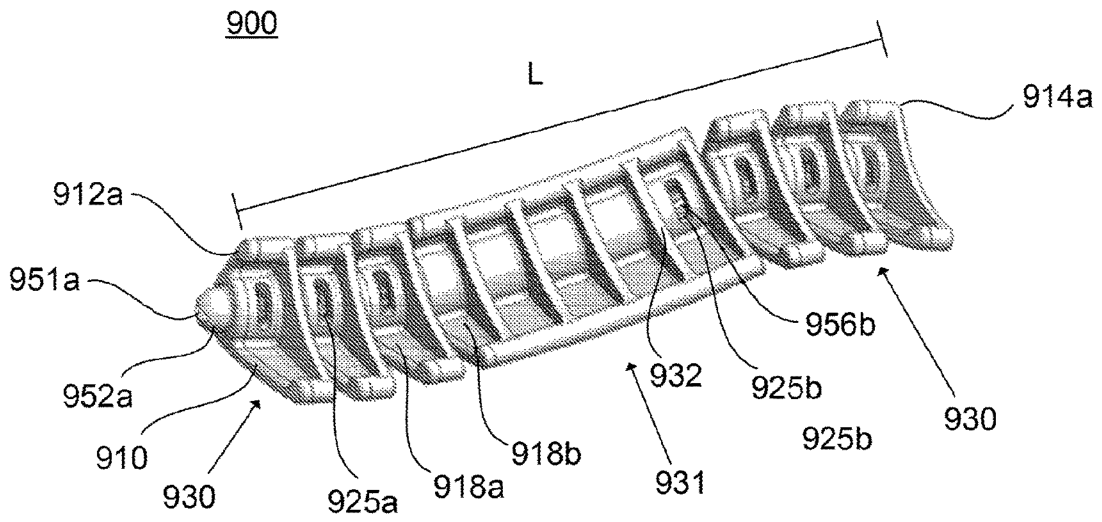
FIG. 10A
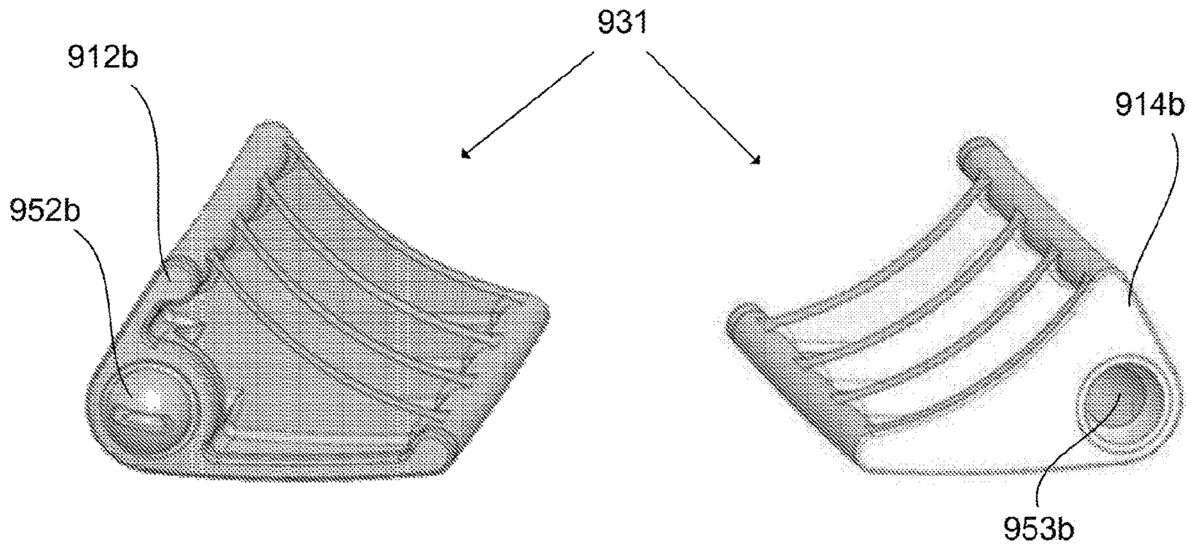
FIG. 10B
FIG. 10C

GRAFT SCAFFOLD

CROSS-REFERENCE TO RELATED APPLICATIONS

The present application is a national phase entry under 35 U.S.C. § 371 of International Application No. PCT/US2019/054030 filed Oct. 1, 2019, the entire disclosure of which is incorporated herein by reference.

FIELD OF THE INVENTION

The invention relates generally to a medical implant, such as a graft scaffold. Methods of using the medical implant is also disclosed.

BACKGROUND OF THE INVENTION

During certain spinal fusion procedures, such as a posterolateral spinal fusion, bone graft material can be placed adjacent transverse processes in the posterolateral portion outside of the spine. The transverse processes are small bony projections on either side of the vertebrae and act as a site of attachment for various muscles and ligaments of the spine. The transverse process is an ideal location for spinal fusion since the area is very vascular and, thus, has increased blood flow. This allows for bone to more easily grow in the region as the higher blood flow transports greater supplies of the requisite nutrients to the area.

When performing spinal fusion bone graft material is often inserted between the adjacent transverse processes using graft scaffolds. However, current scaffolds are inserted without local support and are vulnerable to micromotions as the patient moves. These micromotions can apply forces on the scaffold during the spine's fusing process such that small microfractures may appear along the bone graft material, rather than having a solid and consistent fusion; thus, weakening the spinal fusion and increasing the long-term chance of injury to the patient. Moreover, repetitive micromotions may prevent bone tissue from healing within the region and can lead to an increased nonunion rate.

Thus, it would be preferable for a device that can hold bone graft material while maintaining its position between the adjacent transverse processes in order to facilitate a solid spinal fusion.

BRIEF SUMMARY OF THE INVENTION

The present disclosure is directed to an implant and methods of using the same. The implant can hold bone graft material and receive support from adjacent tissues and structures. In one aspect, the implant has an attachment region to directly engage with adjacent tissues and structures. In another aspect, the implant is malleable and can be manipulated to conform to the adjacent tissues and structures. These implants address the shortcomings of prior art devices and procedures.

In one aspect, an implant comprising an implant comprising a first end and a second end separated from the first end by a length, a window defined between the first end and the second end, a bone graft receiving region in communication with the window, and a first attachment region extending from a first surface of the implant. Further, the implant may include a second attachment region extending from the first surface of the implant. Further, the first attachment region may be adjacent the first end and the second attachment region is adjacent the second end. Further, at least one of the first attachment region and the second attachment region may comprise a plurality of teeth laterally extending from the respective attachment regions. Further, the first surface may include a first porous section between the first attachment region and the second attachment region. Further, the implant may include a second porous section along a second surface of the implant, the first porous section at an angle to the second porous section. Further, the implant may include a hook. Further the hook may be substantially L-shaped. Further, the implant may be substantially triangular. Further, the first end and the second may be curved.

In another aspect, an implant comprising a first end and a second end, the second end being larger than the first end and including a concave surface, a hole formed through the second end, and a first attachment region defined along a surface of the implant. The second end may include a first end surface and the second end includes a second end surface, the second end surface being larger than, and laterally opposite to, the first end surface. The second end surface may define a second attachment region. Further, the concave surface may be between the first end surface and a second end surface. Further, the first attachment region may be adjacent the first end. Further, the concave surface may be shaped to receive a sacral bone. Further, the hole may be defined from a top surface of the implant to the concave surface. Further, the implant may be entirely porous. Further, the first attachment region may be a cut-out extending from a top surface of the implant and extending to a bottom lip of the implant.

In another aspect, a method of use comprising positioning a window of an implant adjacent a transverse process, and securing an attachment region of the implant to a portion of the transverse process, wherein bone is capable of growing from the transverse process through the window. Further, the method may further comprise inserting bone graft material into a bone graft receiving region defined within an implant. Further, the inserting step may include placing bone graft material through a window defined along a length of the implant. Further, positioning the implant may include positioning the implant lateral to a spinous process. Further, securing the attachment region includes pushing the attachment region into the portion of the transverse process. Further, positioning the implant may include positioning a first porous section along a first surface of the implant adjacent the transverse process. Further, positioning the implant may include positioning a second porous section along a second surface of the implant adjacent the transverse process, the second surface including the attachment region and being at an angle transverse to the first surface. Further, positioning the implant may include engaging a first hook of the implant with a portion of a first structure attached to the transverse process. Further, the method may further comprise rotating the first hook about the portion of the first structure. Further, the method may include engaging a second hook of the implant with a second structure attached to the transverse process. Further, positioning the implant may include positioning the implant adjacent an edge of the transverse process. Further, positioning the implant may include positioning the implant perpendicular to a longitudinal axis defined by the transverse process.

In another aspect, a method of use comprising positioning a portion of a sacral bone within a concave surface of an implant, engaging an attachment region of the implant with a portion of a transverse process, and attaching bone graft material to the implant. Further, the method may further comprise inserting a fixation member through a hole formed in the implant. Further, attaching bone graft material to the implant may include laying bone graft material on an exterior surface of the implant and spreading the bone graft material along the exterior surface. Further, engaging the attachment region may include extending a bottom lip of the attachment region past the portion of the transverse process. Further, positioning the implant may include placing a second surface of an end of the implant closer to the portion of the transverse process than a first surface of the end of the implant. Further, positioning the implant may include positioning the portion of the sacral bone within the concave surface of a caudal end of the implant. Further, positioning the implant may include receiving the portion of the transverse process within a medial surface of the implant.

In another aspect, an implant comprising a first end and a second end separated from the first end by a first length extending along a longitudinal axis, and a first malleable portion between the first and second ends capable of moving a section of the medical implant transverse to the longitudinal axis. Further, the implant may further include at least one hole transverse the longitudinal axis and adjacent at least one of the first end and the second end. Further, the at least one hole may include a first hole and a second hole, the first malleable portion lying between the first hole and the second hole. Further, the at least one hole may include a third hole and a fourth hole, wherein the first hole lies between the third hole and the first malleable portion, and the second hole lies between the fourth hole and the first malleable portion, the first and second hole being larger than the third and fourth hole. Further, the implant may further include a bone graft receiving region longitudinally defined through the implant. Further, the implant may further include a flexible member running through the bone graft receiving region of the implant. Further, the flexible member may include a hook on an end of the flexible member, the hook engaged with an exterior surface of the first end. Further, the first malleable portion may additionally be capable of extending implant to a second length greater than the first length. Further, the first malleable portion may comprise a plurality of coils at a transverse angle to the longitudinal axis. Further, the first malleable portion may comprise a plurality of links Further, a first link of the plurality of links may have a first male end configured to be received within a second female end of a second link of the plurality of links and a first female end configured to receive a second male end of a third link of the plurality of links Further, a first link of the plurality of link may include a housing having a sphere rotatably received therein. Further, a second link of the plurality of links may define a receptacle configured to receive a key protruding from the sphere of the first link Further, the key and the sphere may define a first hole, and the receptacle defines a second hole, the first hole being concentric with the second hole. Further, the implant may further include a flexible member running through the first hole and the second hole. Further, the sphere may define two channels and include a ledge therein. Further, the implant may be one of at least one of a straight oblong, curved oblong, or triangular shape. Further, the female end may have a curved surface. Further, the implant may further include a stiff portion having a passage running therethrough, the stiff portion engaged with the first malleable portion. Further, the implant may further include a second malleable portion engaged with the stiff portion, the stiff portion lying between the first malleable portion and the second malleable portion.

In another aspect, a method of use comprising positioning an implant having a first malleable portion adjacent a first transverse process, and manipulating a section of the first malleable portion to conform to a shape of the first transverse process. Further, the method may further comprise bone graft material into a bone graft receiving region defined within the implant. Further, inserting bone graft material may further include inserting the bone graft material through a first window defined along a length of the implant. Further, the first malleable portion may lie between the first window and a second window of the implant, the method further comprising inserting bone graft material through the second window into the bone graft receiving portion. Further, manipulating the portion of the first malleable portion may include at least one of bending or rotating. Further, the method may further comprise implanting a structure within a portion of the first transverse process. Further, manipulating the portion of the first malleable portion may include conforming the first malleable portion to at least one of the first transverse process and the implanted structure. Further, the method may further comprise inserting a fixation member through a hole adjacent an end of the implant. Further, the method may further comprise inserting a first end of a first link of a plurality of links of the first malleable portion within a second end of a second link of the plurality of links of the first malleable portion. Further, the method may further comprise inserting a flexible member through a portion of the implant. Further, inserting the flexible member may include inserting the flexible member through the bone graft receiving portion of the implant, and hooking an end of the flexible member along an external surface of the implant. Further, manipulating the section of the first malleable portion may include manipulating a section of the flexible member. Further, each link of the plurality of links may include a housing rotatably receiving a sphere therein, the method further comprising inserting a key of a first link of the plurality of links into a receptacle of a second link of the plurality of links Further, the sphere may include a key protruding from the sphere, and manipulating the section of the first malleable portion may include manipulating a section of the flexible member, and rotating the sphere within the housing. Further, inserting the flexible member may include inserting two free ends of the flexible member through two channels defined within a sphere protruding from the implant. Further, inserting the flexible member may include engaging a central portion of the flexible member with a ledge of the sphere. Further, the method may further comprise tensioning the flexible member and securing the free ends of the flexible member. Further, each link of the plurality of links may include a panel, and inserting bone graft material includes inserting the bone graft material on an exterior surface of the housing and a surface of the panel. Further, wherein manipulating the section of the first malleable portion may include rotating the first end of the first link about a curved surface of the second end of the first link Further, the method may further comprise placing a stiff portion of the implant between the first transverse process and a second transverse process. Further, the method may further comprise manipulating a second malleable portion of the implant to conform to a shape of the second transverse process. Further, the method may further comprise disengaging an end of the flexible member from the implant and removing the flexible member from the implant. Further, the method may further comprise at least one of adding a link to the plurality of links and removing a link from the plurality of links Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

These and other features, aspects, and advantages of the present invention will become better understood with regard to the following description, and accompanying drawings where:

FIG. 2A is an isometric view of an implant according to another aspect of the invention.

FIG. 2B is a view of the underside of the implant of FIG. 2A.

FIG. 3A is an isometric view of an implant according to another aspect of the invention.

FIG. 7A is an isometric view of an implant according to another aspect of the invention.

FIG. 7B is an isometric view of the implant of FIG. 7A after being manipulated.

FIG. 7C is an isometric view of a male end of a link of the implant of FIG. 7A.

FIG. 7D is an isometric view of a female end of a link of the implant of FIG. 7A.

FIG. 10A is an isometric view of an implant according to another aspect of the invention.

FIG. 10B is an end view of a male end of a stiff portion of the implant of FIG. 10A.

FIG. 10C is an end view of a female end of the stiff portion of the implant of FIG. 10A.

DETAILED DESCRIPTION

Figure 1A:
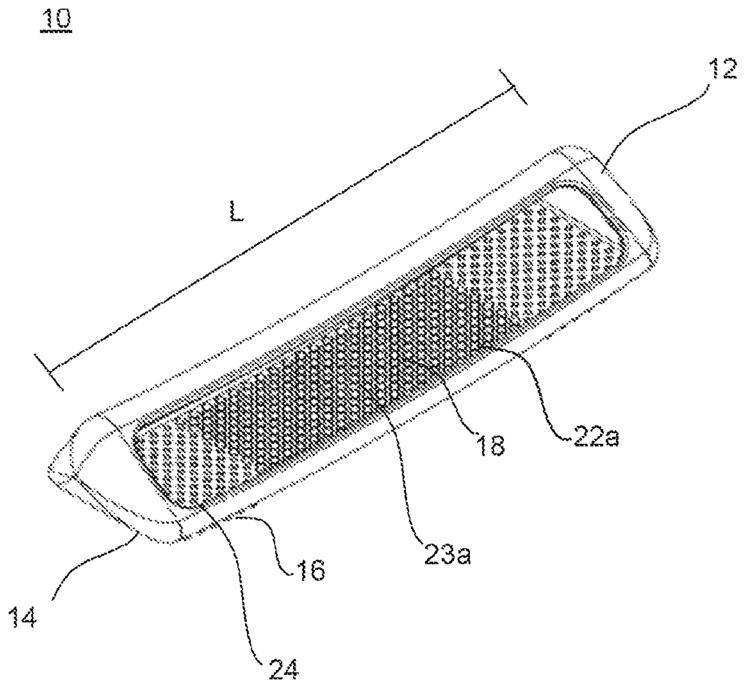
FIG. 1A is an isometric view of an implant according to an aspect of the invention.
Figure 1B:
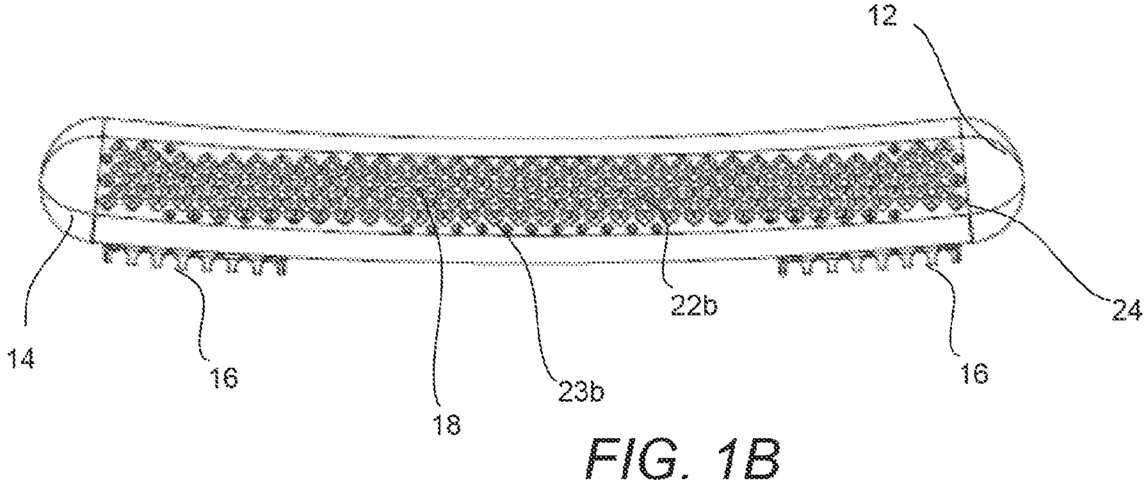
FIG. 1B is a side view of the implant of FIG. 1A.
Figure 1C:
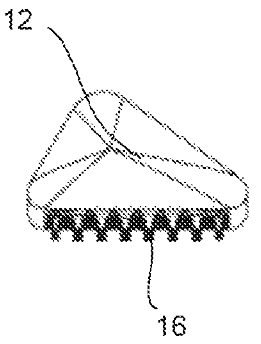
FIG. 1C is an end view of the implant of FIG. 1A.

Various embodiments will now be described in detail with reference to the drawings, wherein like reference numerals identify similar or identical elements. Additionally, in the drawings and in the description that follows, terms such as front, rear, upper, lower, top, bottom, and the similar directional terms are used simply for convenience of description and are not intended to limit the disclosure attached hereto.

In the drawings and description that follows, the term "proximal" refers to the portion of the device that is closest to the operator, while the term "distal" refers to the portion of the device that is furthest from the operator. The term "cephalad" is used to indicate a direction toward a patient's head, whereas the term "caudal" indicates a direction toward the patient's feet. The term "medial" indicates a direction toward the middle of the body of the patient, while the term "lateral" indicates a direction toward a side of the body of the patient (i.e., away from the middle of the body of the patient). The term "posterior" indicates a direction toward the patient's back, and the term "anterior" indicates a direction toward the patient's front. In the following description, well-known functions or constructions are not described in detail to avoid obscuring the present disclosure in unnecessary detail.

Figure 1D:
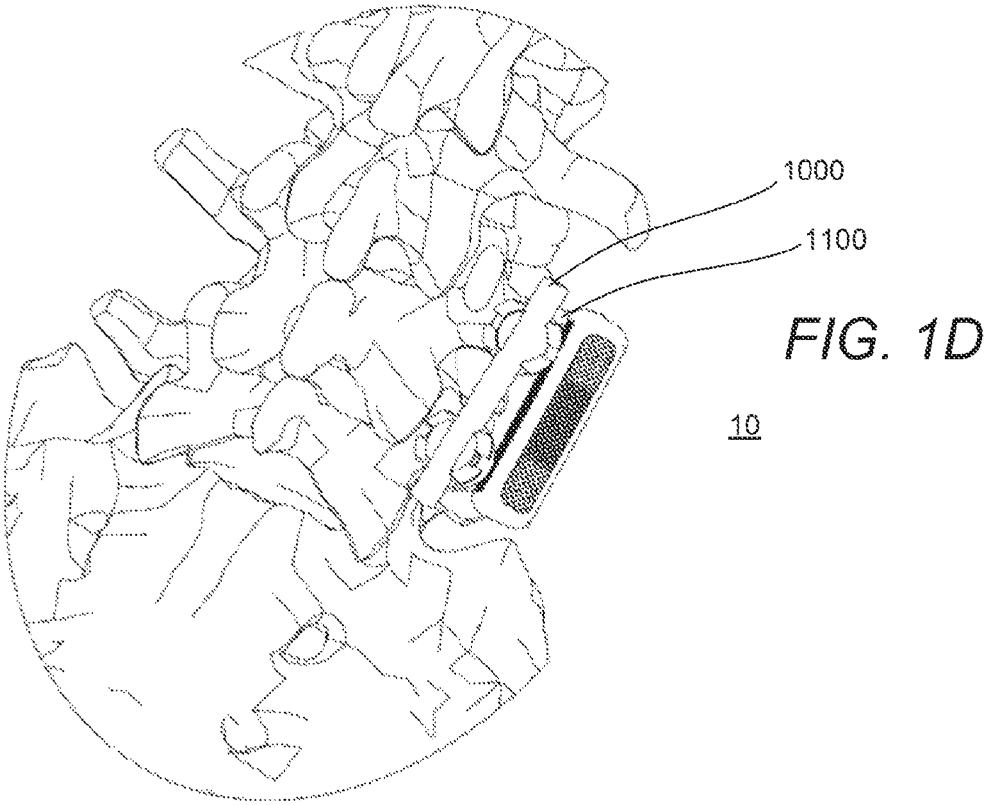
FIG. 1D illustrates the implant of FIG. 1A implanted on adjacent vertebrae.
Figure 1E:
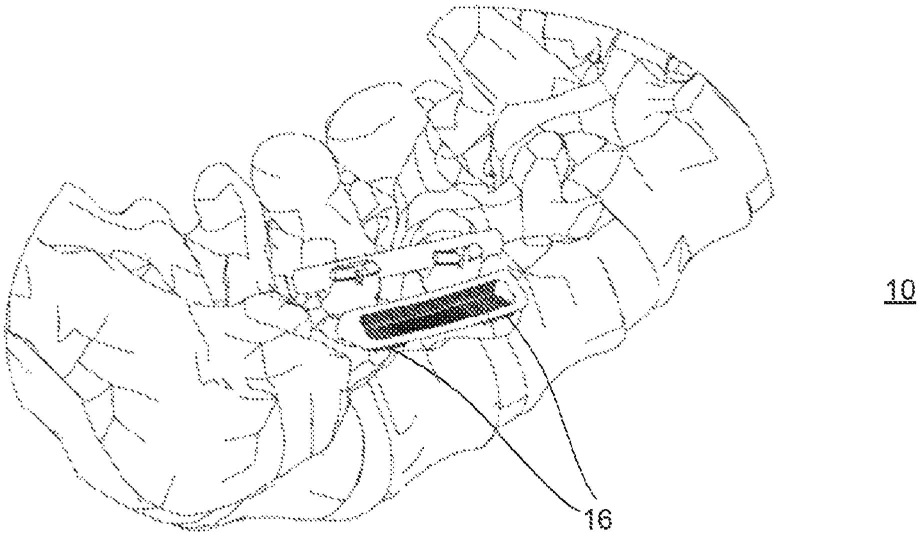
FIG. 1E is another illustration of the implant of FIG. 1A implanted on adjacent vertebrae.

FIGS. 1A-1E illustrates an implant 10 with a length L extending between a first end 12 and a second or caudal end 14, attachment regions 16, a bone graft receiving region 18, and porous sections 22*a*, 22*b*. Implant 10 has a tubular triangular shape with ends 12, 14 each having a smooth and curved shape. However, in alternative aspects, implant 10 can be configured and dimensioned in any shape or size that facilitates the retention of bone graft material, and can have any other shape (e.g., rectangular, triangular, or any other geometric or non-geometric shape). For example, a thickness and/or width of implant 10 can be lowered in order to minimize at least one of a lateral or vertical profile implant 10. In a further alternative aspect, ends 12, 14 do not mirror each other, and may each have a unique shape and dimension, as shown in FIGS. 2A-3C. In yet another alternative aspect, ends 12, 14 can each include a window (not shown) to facilitate insertion of bone graft material into medical implant 10. FIGS. 1D-1E depicts implant 10 resting adjacent transverse processes such that ends 12, 14 extends both between and beyond the transverse processes. In an alternative aspect, length L can include a distance over multiple transverse processes of adjacent vertebrae, such as three, four, or any number of vertebrae.

Attachment regions 16 extends from an exterior surface of implant 10 along either side of a first porous section 22*a* and includes a plurality of teeth configured to engage adjacent structure, such as osseous tissue (e.g., transverse processes, or any other bony tissue along the spine). In this manner, implant 10 can be given greater support from adjacent structures during spinal fusion by minimizing micromotions after implant 10 has been inserted within the patient. This increase in stability will give the patient's body a more secure area for bone growth while decreasing the chance of microfractures appearing along the healed spinal fusion. In alternative aspects, attachment regions 16 can have other means of engaging adjacent tissue, such as spikes, resilient jaws, or other means of assisting in limiting migration of implant 10. In a further alternative aspect, attachment regions 16 do not each have the same formation, and each can have a unique and distinct shape. Although FIGS. 1A-E depicts implant 10 having two attachment regions 16, alternative aspects may include only one, three, four, or any number of attachment regions 16. In a further alternative aspect, attachment regions 16 may extend from a porous section 22*b*. Alternatively, attachment regions 16 can extend from both porous sections 22*a*, 22*b*.

Bone graft receiving region 18 is defined along a portion of length L within implant 10. Bone graft receiving portion 18 is configured to facilitate receiving and holding a bone graft material. In a further alternative aspect, bone graft receiving region 18 can run the entire length L of implant 10 rather than only a portion thereof. Window 24 is defined along a portion of length L, but shorter in length than bone graft receiving region 18, and provides access to bone graft receiving portion 18. In an alternative aspect, window 24 may have any length or shape, and may be placed along any portion of implant 10, so long as window 24 provides access to bone graft receiving portion 18. For instance, window 24 may be a small circle placed off-center of a surface of implant 10 (e.g., adjacent either of ends 12, 14). Moreover, there may be any number of windows, such as two, three, four, or the like.

Figure 3B:
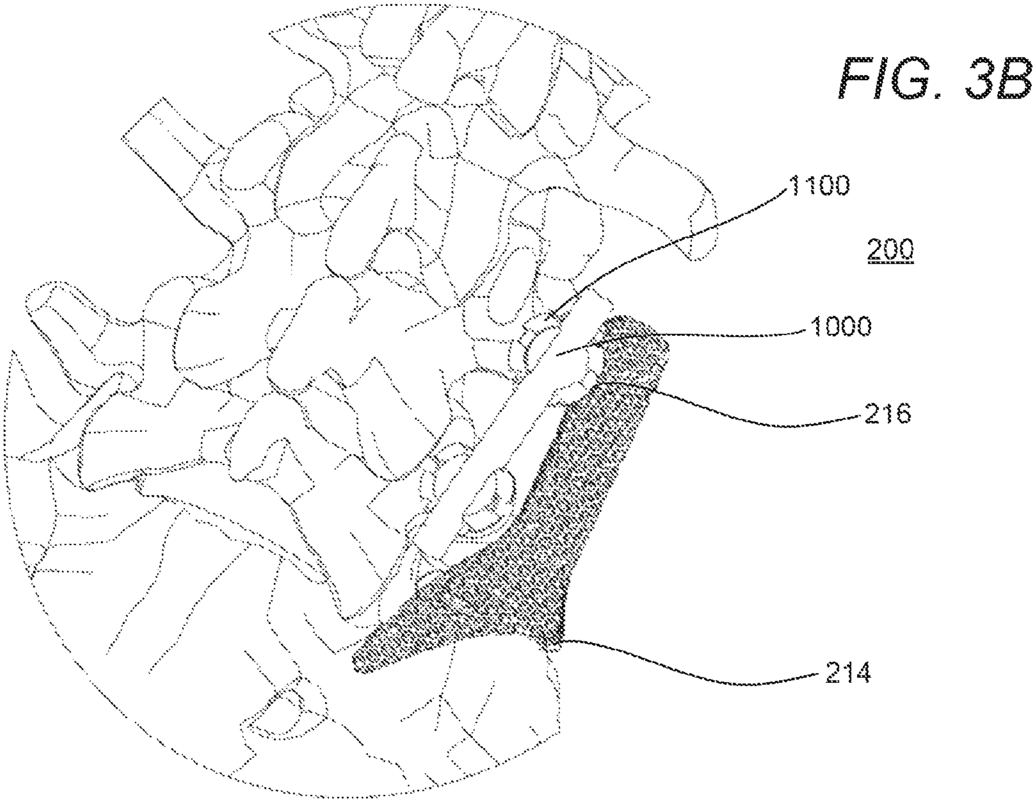
FIG. 3B illustrates the implant of FIG. 3A inserted on adjacent vertebrae.
Figure 3C:
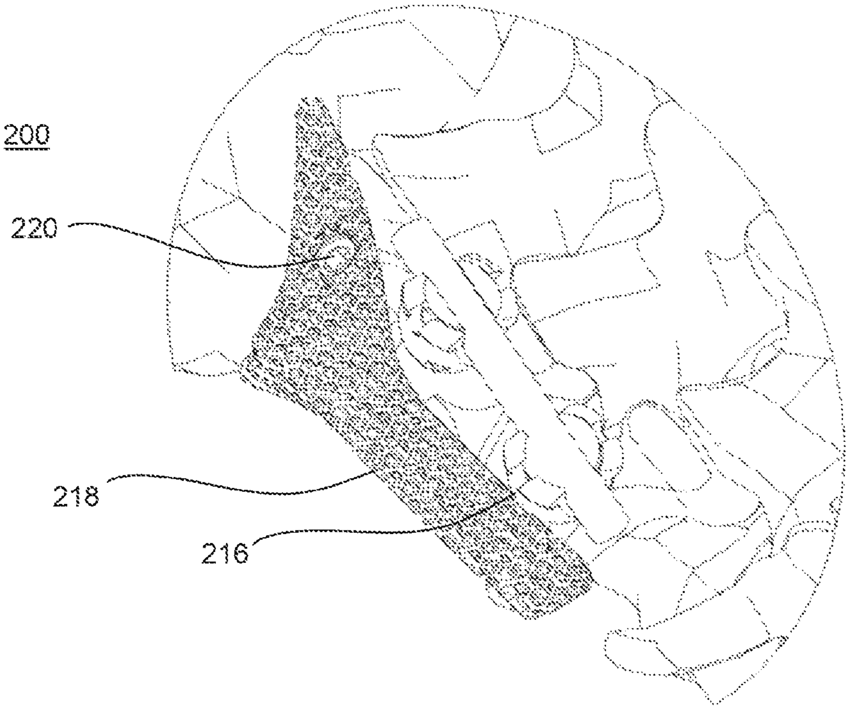
FIG. 3C is another illustration of the implant of FIG. 3A inserted on adjacent vertebrae.

Implant 10 includes porous section 22*a* along a first surface of implant 10 and porous section 22*b* along a second surface of implant 10. Due to the triangular construction of implant 10, porous section 22*a* is at an angle to porous section 22*b*. Porous section 22*b* is longer than porous section 22*a* as attachment regions 16 lie on either side of porous section 22*a*, taking up a portion of the first surface of implant 10, meanwhile porous section 22*b* does not have an attachment region and runs the entire length of the first surface. In an alternative aspect, porous sections 22*a*, 22*b* can have an equal length. In a further alternative aspect, porous section 22*a* is longer than porous section 22*b*. Porous sections 22*a*, 22*b* includes a plurality of pores 23*a*, 23*b* running along the respective porous sections 22*a*, 22*b*. Pores 23*a*, 23*b* extend from bone graft receiving portion 18 through the respective first and second surfaces of implant 10. Pores 23*a*, 23*b* are sized to promote bone growth into and through implant 10. Pores 23*a*, 23*b* have a circular shape to mimic bone growth along Haversian canals and lamellar structures of bone. Moreover, pores 23*a*, 23*b* reduces the density and stiffness of implant 10 while allowing more space for bone graft material to be inserted. Pores 23*a*, 23*b* can have a diameter in the range of about 50-1000 μm, although alternative aspects may include a larger or smaller diameter, with each pore distanced from each other by a distance of 0.10-50 μm. In alternative aspects, pores 23*a*, 23*b* are not circular and can have any other shape (e.g., rectangular, triangular, or any other geometric shape) including non-geometric shapes such as a random porosity generated through additive manufacturing, described further below. In a further alternative aspect, a first portion of either of porous sections 22*a*, 22*b* may have a first set of pores having a first shape (e.g., circular) while a second portion of porous section 22*a*, 22*b* may have a second set of pores having a second, different shape (e.g., rectangular). In a further aspect, pores 23*a* can have a different shape and/or size compared to pores 23*b*. Alternatively, the entirety of implant 10 may be composed of pores 23, rather than just porous section 22, as shown in FIGS. 3A-3C.

FIGS. 2A-2B illustrates an implant 100 according to another aspect of the disclosure. Implant 100 is similar to implant 10 detailed above with similar structures represented with reference numerals including an additional "1" preceding the previous reference numeral. Similar features will not be discussed in detail for reasons of brevity. In this aspect, second end 114 has larger height and width than first end 112. Second end 114 is configured and dimensioned to contour to an adjacent vertebrae or osseous tissue. In this manner, the points of contact between second end 114 and adjacent tissue may be maximized to provide better spinal fusion. Second end 114 includes a concave surface to engage an adjacent bone, such as a sacral bone. Second end has a first surface 115 laterally opposite, and having a lesser surface area than, second surface 117. As second surface 117 is medial to first surface 115, the larger surface area of second surface 117 allows second surface 117 to have greater contact with adjacent tissues, such as nearby transverse processes. In an alternative aspect, surfaces 115, 117 can have an equal surface area. Alternatively, first surface 115 can have a greater surface area than second surface 117. Second end 114 has a hole 120 running from an exterior surface second end 114 through to the concave surface of second end 114. Hole 120 is configured and dimensioned to receive a fixation member (not shown), such as a bone screw, to provide greater support and stability to implant 100 during spinal fusion. Alternatively or additionally, bone graft material may be inserted within hole 120.

Medial surface 119 is a flat surface and is laterally opposite a lateral edge of implant 100. Medial surface 119 allows for implant 100 to have greater contact points with adjacent tissue while the opposite lateral edge decreases the vertical profile of implant 100 while the lateral edge lowers the profile of implant 100. Bone graft receiving portion 118 is a flat, top surface of implant 100 along length L capable of receiving bone graft material. In alternative aspects, bone graft receiving portion 118 may be a portion defined within implant 100, similar to implant 10.

Attachment regions 116*a*, 116*b* are cut-outs along a medial surface of implant 100. Attachment region 116*a* is adjacent first end 112 and has a smaller surface area than attachment region 116*b*. In this manner, the larger surface area of attachment region 116*b* corresponds with the larger surface area of second surface 117 to similarly allow for greater contact with adjacent tissues, as described above. In alternative aspects, attachment region 116*b* can have a surface area equal to or less than that of attachment region 116*a*. Attachment regions 116*a* 116*b* are both cut out from a top surface of implant 100 without being cut through a bottom surface of implant 100 such that attachment regions 116*a*, 116*b* form a cup-like formation with a bottom lip. This allows for attachment regions 116*a*, 116*b* to partially encompass adjacent tissues that may be laterally protruding, such as a transverse process, so that the bottom lip of attachment regions 116*a*, 116*b* and a bottom surface of implant 100 medially extends past the adjacent tissue. In this manner, attachment regions 116*a*, 116*b* can maximize the points of contact between the transverse process and implant 100 to allow for maximal bone growth. Similar to attachment regions 16 as depicted in FIGS. 1A-1E, the cut-out configuration of attachment regions 116*a*, 116*b* also assists in limiting migration of implant 100 but is able to provide a smaller profile than that of implant 10. In alternative aspects, attachment regions 116*a*, 116*b* can be cut out from the top surface of implant 100 entirely through to the bottom surface of implant 100. Alternatively, attachment regions 116*a*, 116*b* can be cut out from the bottom surface of implant 100 without going through the top surface of implant 100, thus leaving a top lip. In yet further aspects, attachment regions 116*a*, 116*b* are cut out of a middle portion of the medial surface of implant 100 without going through a top or bottom surface of implant 100. In a yet further aspect, there may be only one attachment region cut out along a length of implant 100. Although attachment regions 116*a*, 116*b* are depicted as predominantly rectangular, other aspects may have attachment regions 116*a*, 116*b* be any shape (e.g., rectangular, triangular, or any other geometric or non-geometric shape).

In an alternative aspect, implant 10, 100 can be entirely porous. In this manner, a more complete bone growth may be promoted throughout the entirety of implant 10, 100. For example, FIGS. 3A-3B illustrates implant 200 according to another aspect of the disclosure. Implant 200 is similar to implants 10, 100 detailed above with similar structures represented with reference numerals including a “2” preceding the previous reference numeral. Similar features will not be discussed in detail for reasons of brevity. In this aspect, implant 200 retains a structure similar to implant 100, described above, but is composed entirely of pores 223 to allow for bone to grow through implant 200 while still maintaining the structural benefits of being engaged to surrounding tissue through attachment region 216. Although pores 223 are depicted as being offset from each other throughout implant 200, in alternative aspects, pores 223 may be concentrically aligned with each other. In a further alternative aspect, implant 200 can be composed of multiple portions, each having a set of pores 223 with differing shapes and/or sizes. For instance, an outer layer of implant 200 can have a first porosity (e.g., with a smaller diameter and of a circular shape) while an inner section of implant 200 can have a second, differing porosity (e.g., with a larger diameter and of a rectangular shape).

Figure 4A:
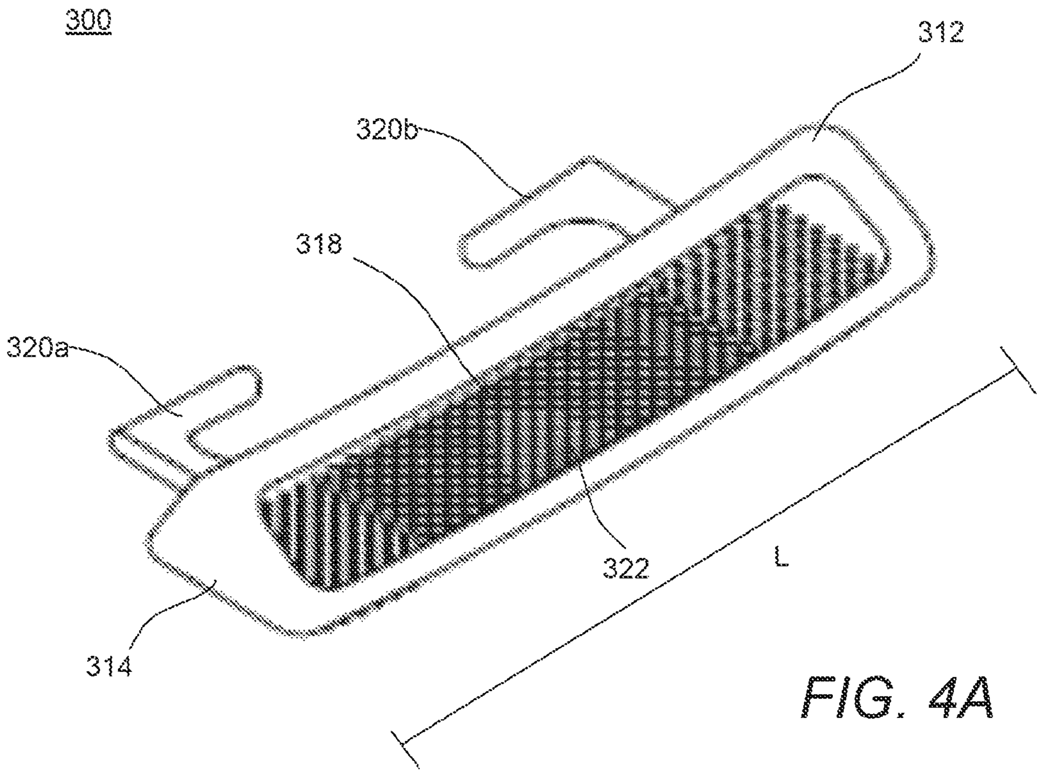
FIG. 4A is an isometric view of an implant according to another aspect of the invention.
Figure 4B:
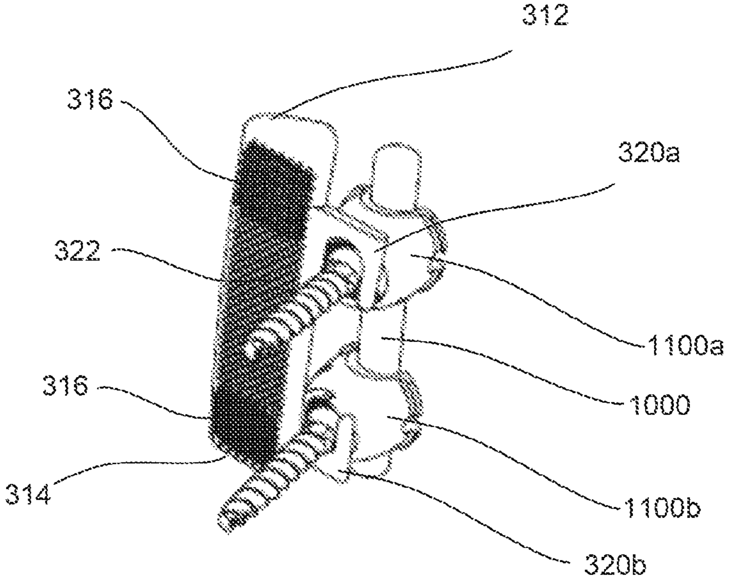
FIG. 4B illustrates the implant of FIG. 4A attached to hardware according to an aspect of the invention.

FIGS. 4A-4B illustrates implant 300 according to another aspect of the disclosure. Implant 300 is similar to implants 10, 100, 200 detailed above with similar structures represented with reference numerals including a “3” preceding the previous reference numeral. Similar features will not be discussed in detail for reasons of brevity. In this aspect, implant 300 includes hooks, 320*a*, 320*b*. Hooks 320*a*, 320*b* are substantially L-shaped such that a first leg extends perpendicularly from implant 300 while a second leg perpendicularly extends from the first portion and parallel to implant 300, with the second leg extending towards a center of implant 300. In alternative aspects, hooks 320*a*, 320*b* can be any shape, including being curved, having the legs of the hook be at a variety of angles from each other and/or implant 300 (e.g., 45 degrees between the first legs and the second leg of the hook, 60 degrees between the first leg of the hook and implant 300, or the like), or any other orientation that allows hooks 320*a*, 320*b* to engage with adjacent structures. Hooks 320*a*, 320*b* are configured and dimensioned to attach implant 300 to adjacent implanted structure. FIG. 4B depicts hooks 320*a*, 320*b* engaged around a shaft, and under a tulip head, of respective bone screws 1100*a*, 1100*b* to secure implant 300. Alternatively, in other aspects, hooks 320*a*, 320*b* can be secured to rods 1000. In a further alternative aspect, each of hooks 320*a*, 320*b* can be hooked onto different implanted structure. For example, a first hook 320*a* can be hooked onto rod 1000 while a second hook 320*b* can be hooked onto bone screw 1100. In a yet further alternative aspect, hooks 320*a*, 320*b* can be secured over adjacent vertebra. In another aspect, hooks 320*a*, 320*b* can be a slot through which a flexible band (not shown) is passed for attachment to adjacent implanted structures.

An exemplary method of use will now be discussed with reference to implant 10, as shown in FIGS. 1A-1E. Once a working portal or area has been created on a patient, a surgeon inserts implant 10 within the patient. As depicted in FIGS. 1D and 1E, implant 10 is positioned lateral of the spinous process, adjacent edges of transverse processes of adjacent vertebrae, and perpendicular to the transverse process. Although implant 10 is depicted as also being positioned laterally to both of the transverse processes, and the adjacent implanted structures of rod 1000 and bone screw 1100, in alternative aspects, implant 10 may be positioned adjacent only one of either the transverse processes or the implanted structures. In a further alternative method of use, implant 10 is not limited to being positioned adjacent the edges of the transverse process, but may be positioned along any portion of the transverse process. In a yet further alternative method of use, implant 10 may be placed at any angle with respect to the transverse process, such as being longitudinally aligned with the transverse process, 45 degrees with respect to the transverse process, or at any position desired by the surgeon. Once implant 10 has been placed into position, implant 10 may be secured to adjacent tissue, such as osseous tissue, through attachment regions 16. For example, where attachment regions 16 are a set of teeth or spikes (not shown) the surgeon may push or hammer attachment regions 16 into adjacent tissue to limit movement of implant 10. Either before or after the surgeon secures implant 10 to adjacent tissue, bone graft material may be inserted within bone graft receiving portion 18 through window 24.

In another method of use, FIGS. 3B-3C depicts implant 200 being secured to adjacent tissue and implant structures. In this method, after an incision in the patient is made and implant 200 has been positioned within the patient as described above, implant 200 is adjusted until a concave surface of second end 214 is placed against and receives adjacent tissue, such as a portion of a sacral bone, in such a manner as to maximize the points of contact between end 210 and the adjacent tissue. Implant 200 is additionally maneuvered such that attachment region 216 receives a portion of a transverse process. A bone screw is then inserted within hole 220 to secure implant 200 to the patient. In an alternative aspect, a bone screw is not inserted within hole 220 and, instead, bone graft material may be inserted within hole 220 instead. Alternatively, both bone graft material and a bone screw can be inserted into hole 220. Either before or after the surgeon secures implant 200 to adjacent tissue, bone graft material may be attached to implant 200. This may include laying the bone graft material on bone graft receiving portion 218 and spreading the material along a portion thereof. Although FIGS. 3B-3C illustrates implant 200 in use, implant 100 may also be used with the described method due to the shared structural similarities between implant 100 and implant 200.

In another method of use, FIG. 4B depicts implant 300 being secured to adjacent bone screws 1100 through hooks 320*a*, 320*b*. In this method, after an incision in the patient is made and implant 300 has been inserted within the patient as described above, a first hook 320*a* receives a portion of a first bone screw 1100*a* therein, with implant 300 being at an angle transverse to a longitudinal axis defined between bone screws 1100*a*, 1100*b*. Implant 300 is then axially moved to further receive first bone screw 1100*a* within first hook 320*a* so that, when implant 300 is rotated about first bone screw 1100*a*, there is sufficient clearance to align a second hook 320*b* with a second bone screw 1100*b* without a tip of second hook 320*b* colliding with bone screw 1100*b* while implant 300 is rotated. Implant 300 is then rotated about first bone screw 1100*a* to align second hook 320*b* with second bone screw 1100*b*. Implant 300 is then axially adjusted so that both bone screws 1100*a*, 1100*b* is securedly engaged within hooks 320*a*, 320*b*. In alternative aspects, either or both of hooks 320*a*, 320*b* can engage with other implanted structures, such as rod 1000, and/or adjacent tissue, such as a transverse process. Implant 300 is then secured to adjacent osseous tissue through attachment regions 316, similar to the method of implanting implant 10, above.

Although implants 10, 100, 200, 300 can derive additional support for spinal fusion by attaching to adjacent structures, alternative aspects may include implants that derive support through having their shape molded along the transverse process and adjacent implanted structures. In this manner, an implant can receive support during spinal fusion through sitting along and adjacent to nearby structures, such as the vertebral structures of the transverse process and/or adjacent spinal implants, to create an initial hold on the spine before muscles are laid on top of the implant. Although not required, such a malleable implant may additionally include an attachment region as previously described. Moreover, the implant's malleability may allow for greater customization to a patient's specific vertebral geometry in addition to more efficiently utilizing the available space within a patient.

Figure 5:
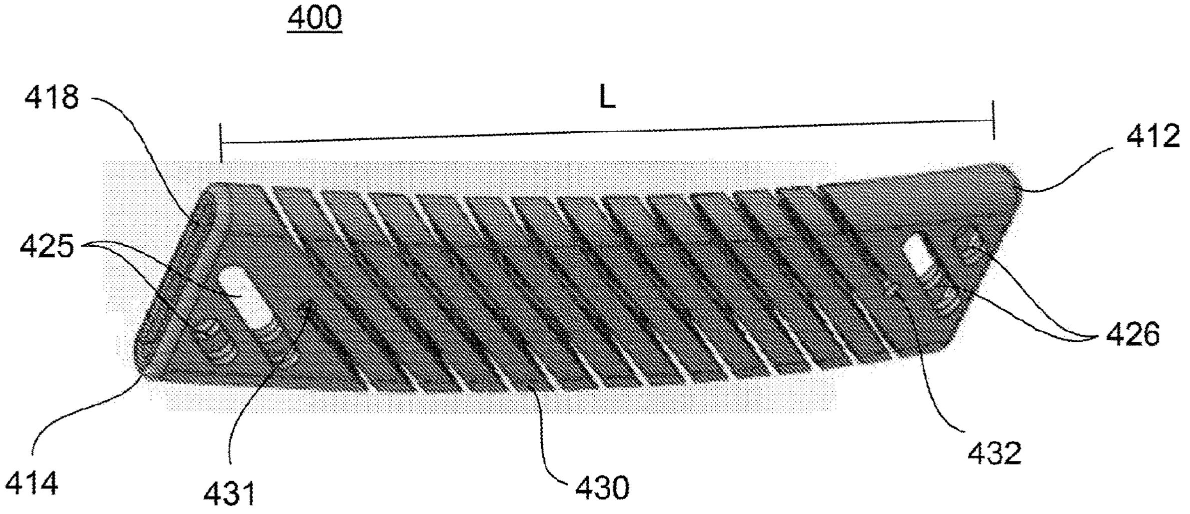
FIG. 5 is an isometric view of an implant according to another aspect of the invention.

FIG. 5 illustrates an implant 400 according to another aspect of the disclosure. Implant 400 is similar to implants 10, 100, 200, 300 detailed above with similar structures represented with reference numerals include a "4" preceding the previous reference numeral. In this aspect, implant 400 has a substantially oblong shape defining a bone graft receiving portion 418 for receiving bone graft. Adjacent ends 412, 414 are respective windows 425, 426 defined through medical implant 400 and transverse to a longitudinal axis defined by implant 400. Windows 425, 426 have a substantially oblong shape and aid in allowing a surgeon to insert bone graft material within bone graft receiving portion 418. Each of windows 425, 426 have a longer and shorter window such that the surgeon may have more access to insert bone graft material within bone graft receiving portion 418. In alternative aspects, there may be any number of windows along implant 400 (e.g., one, three, four, five, or any number of windows) and each window may have equal lengths. Further alternative aspects may include either or both of implant 400 and windows 425, 426 being another shape (e.g., rectangular, triangular, or any other geometric or non-geometric shape).

Implant 400 includes a malleable portion 330 defined between first point 431 and second point 432. Malleable portion 430 is a plurality of coils cut out along implant 400 such that a surgeon may adjust the length of implant 400 to be longer than length L despite being made of a rigid material. The coil-like shape of malleable portion 430 is cut in a transverse angle to the longitudinal axis defined by implant 400 to maximize the number of coils along malleable portion 430 and increase the malleability of implant 400. Malleable portion 430 additionally allows a surgeon to manipulate implant 430 by bending a section of malleable portion 430 in a direction transverse to, or rotated about, a longitudinal axis defined by length L. In this manner, a surgeon may conform implant 400 to a patient's specific vertebral geometry and/or nearby implanted structures; thus, receiving support from adjacent structures during bone fusion. This manipulation may be done before or after placing implant 400 adjacent the vertebral or implanted structures. In alternative aspects, implant 400 can include an attachment region (not shown) similar to attachment regions 16, 116*a*, 116*b*, 216, 316, described above, to provide additional support during bone fusion by attaching to adjacent tissue, such as osseous tissue.

Figure 6:
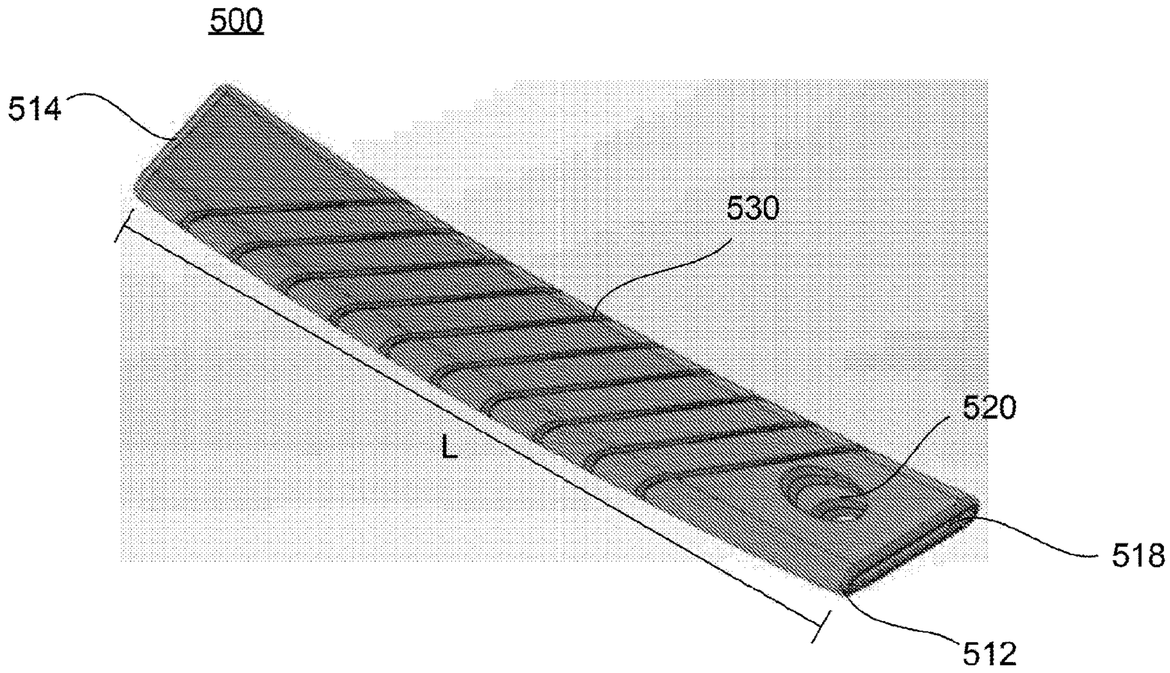
FIG. 6 is an isometric view of an implant according to another aspect of the invention.

FIG. 6 illustrates an implant 500 according to another aspect of the disclosure. Implant 500 is similar to implants 10, 100, 200, 300, 400 detailed above with similar structures represented with reference numerals include a "5" preceding the previous reference numeral. Similar features will not be discussed in detail for reasons of brevity. In this aspect, implant 500 includes a hole 520 defined through a depth of medical implant 500 and transverse to a longitudinal axis defined by length L. Hole 520 can be configured and dimensioned to receive a fixation member, such as a bone screw (not shown). Hole 520 may also serve as an access point for a surgeon to insert bone graft material. In alternative aspects, there may be more than one hole 520, each of which can be located on implant 400 along any point of length L, such as having one hole adjacent each of ends 512, 514.

Figure 7E:
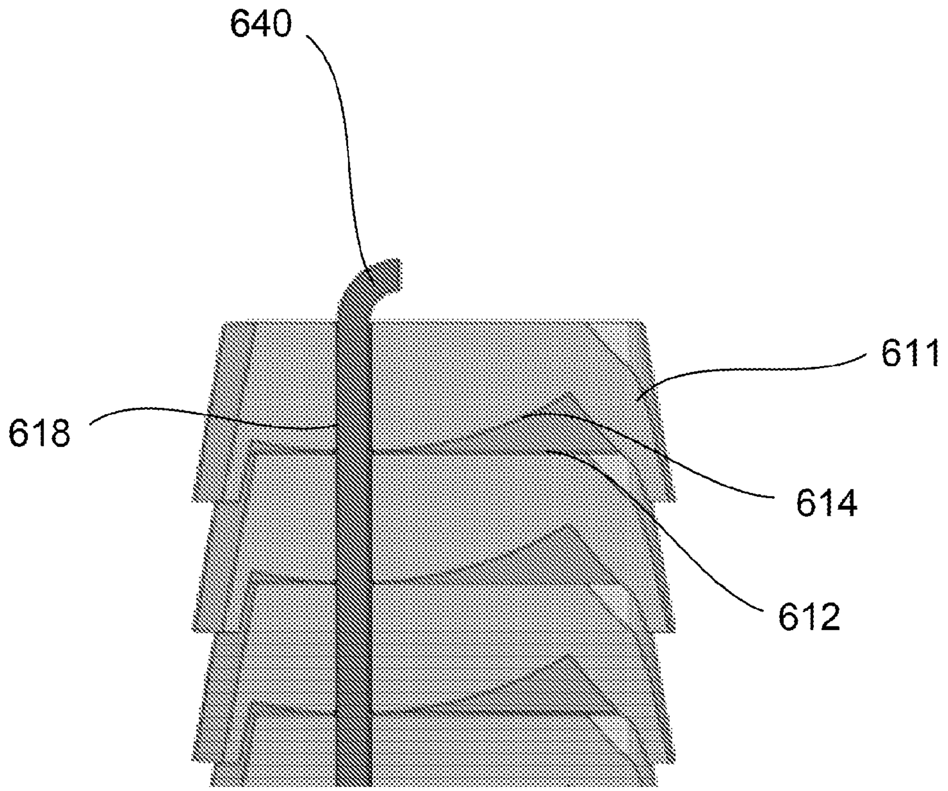
FIG. 7E is a cross-sectional view of the implant of FIG. 7A.
Figure 7F:
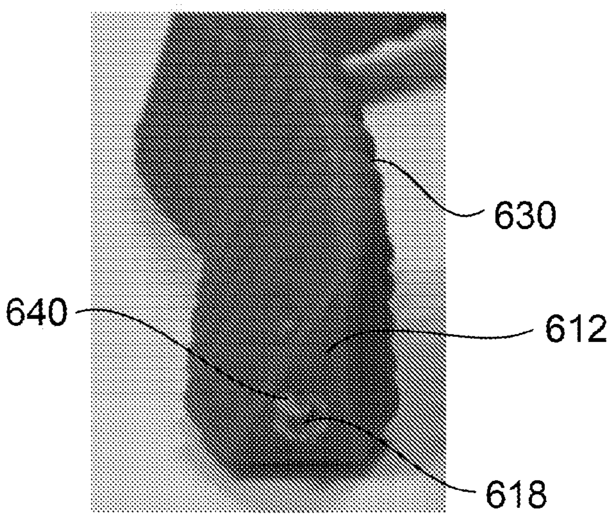
FIG. 7F is an end view of the implant of FIG. 7A.
Figure 8:
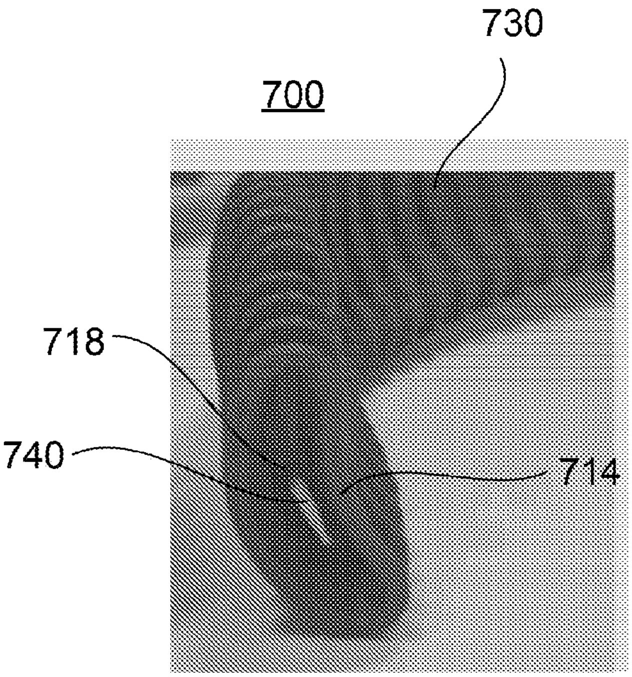
FIG. 8 is an isometric view of an implant according to another aspect of the invention.

FIGS. 7A-7F illustrates an implant 600 according to another aspect of the disclosure. Implant 600 is similar to implants 10, 100, 200, 300, 400, 500 detailed above with similar structures represented with reference numerals include a "6" preceding the previous reference numeral. Similar features will not be discussed in detail for reasons of brevity. In this aspect, implant 600 is a substantially triangular shape. As depicted in FIG. 7A, malleable portion 630 runs the entire length of implant 600 such that a surgeon may have greater freedom to manipulate implant 600. Malleable portion 630 is a set of links 610 keyed within each other. As depicted in FIGS. 7C-7E, each link 610 has a male end 612, and a female end 614 defined by walls 611, which themselves have curved surfaces. Female end 614 is sized and shaped to receive male end 612 of an adjacent link such that each male end 612 can be keyed into a female end 614 of an adjacent link to form malleable portion 630. Moreover, female end 614 has a curved surface configured to allow male end 612 of an adjacent link 610 to rotate along the curved surface of female end 614 when a section of malleable portion 630 is manipulated by the surgeon. Malleable portion 630 is supported by a flexible member 640 running the length of medical implant 600. Bone graft receiving portion 618 can be accessed through windows 625 adjacent end 614. Flexible member 640 sits within bone graft receiving portion 618 and is manipulated in a similar manner to malleable portion 630 to match the shape of malleable portion 630. Flexible member 640 can be made out of any biocompatible material that is capable of being adjusted while also providing structural support to implant 600, such as nitinol, commercially pure titanium, titanium alloy, stainless steel, cobalt-chrome, or the like. FIG. 7B depicts implant 600 after malleable portion 630 has been manipulated. As depicted in FIG. 7C, flexible member 640 also includes a hook engaging a portion of an exterior surface of ends 612, 614 to assist in maintaining the placement of flexible member 640 within implant 600. In this manner, flexible member 640, and the hooks on each end of flexible member 640, allows the links of malleable portion 630 to remain keyed within each other without falling out. FIG. 8 illustrates an implant 700 similar to implant 600. In this aspect, implant 700 has a banana-like or a curved oblong shape. Implants 600, 700 may alternatively have other shapes (e.g., rectangular, hexagonal, or any other geometric or non-geometric shape).

Figure 9A:
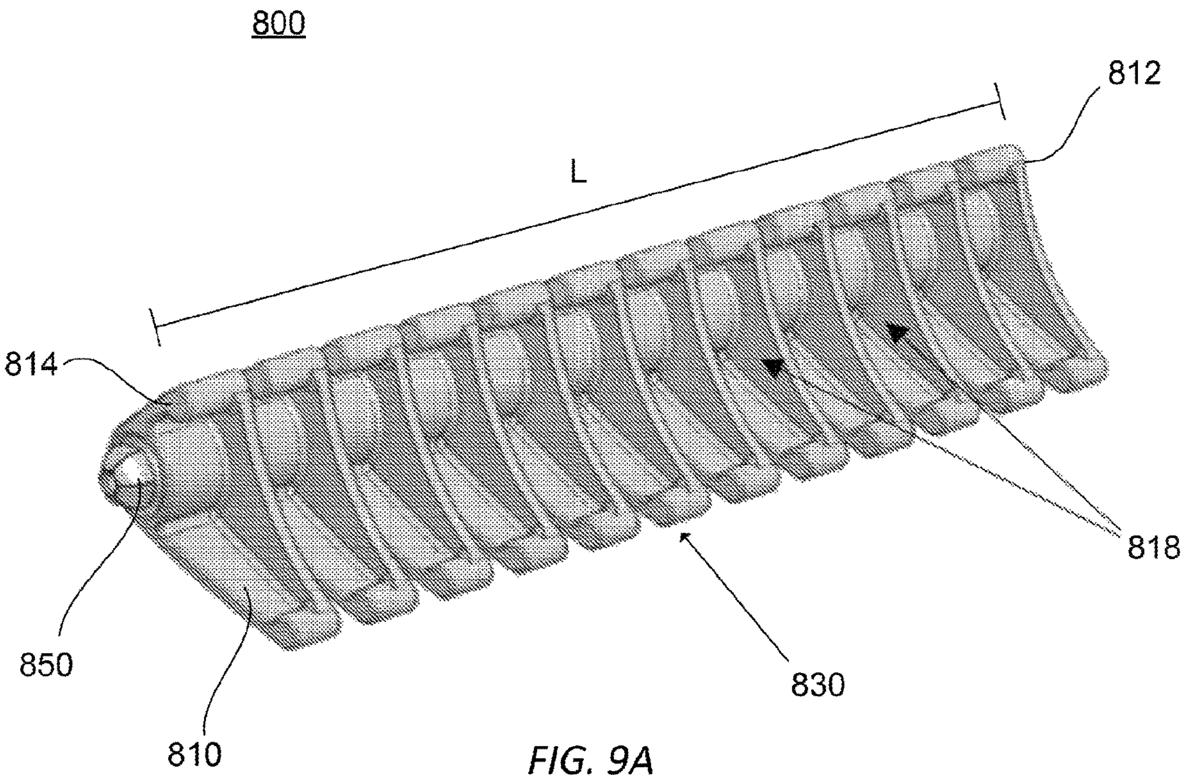
FIG. 9A is an isometric view of an implant according to another aspect of the invention.
Figure 9B:
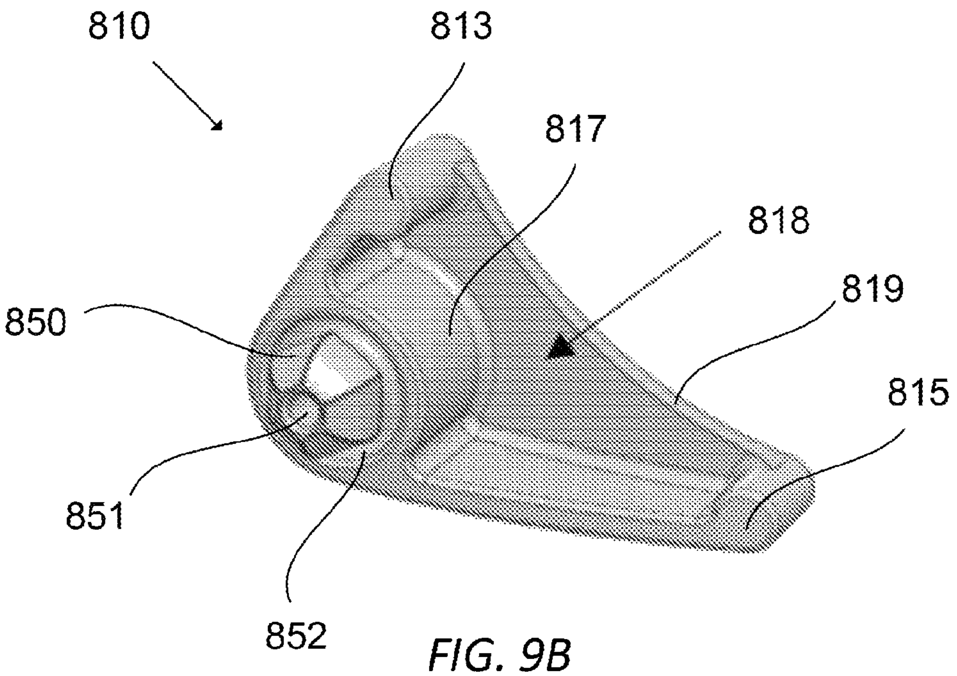
FIG. 9B is an isometric view of a link of the implant of FIG. 9A.
Figure 9C:
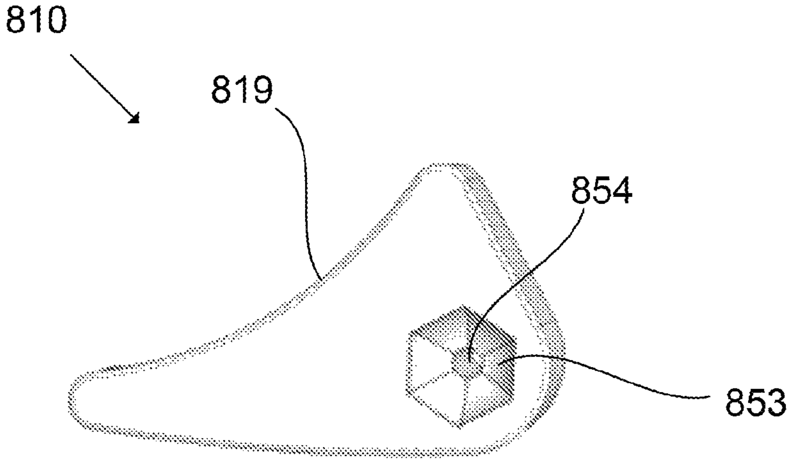
FIG. 9C is a rear view of the link of FIG. 9B.

FIGS. 9A-9C illustrates an implant 800 according to another aspect of the disclosure. Implant 800 is similar to implants 10, 100, 200, 300, 400, 500, 600, 700 detailed above with similar structures represented with reference numerals include an "8" preceding the previous reference numeral. Similar features will not be discussed in detail for reasons of brevity. In this aspect, as depicted in FIG. 9A, implant 800 is substantially triangular with a malleable portion 830 made up of a set of links 810 attached to each other. As depicted in FIG. 9B, each link 810 has ends 813, 815 and a housing 817 having a sphere 852 received therein. Ends 813, 815, a front surface of panel 819, and an exterior of housing 817 defines a graft receiving portion 818 for a surgeon to insert bone graft material within. Panel 818 has a curved edge running between ends 813, 815. However, in alternative aspects, panel 818 may have a straight edge. Although ends 813, 815 are depicted as round and bulbous, in alternative aspects, ends 813, 815 may be any shape (e.g., rectangular, triangular, or any other geometric or non-geometric shape). An interior of housing 817 is sized to rotatably receive sphere 852. Key 850 protrudes from sphere 852 and has a substantially hexagonal shape. In alternative aspects, key 850 may be another shape (e.g., rectangular, triangular, or any other geometric or non-geometric shape). Key 850 and sphere 852 defines an opening 851 such that a malleable flexible member (not shown), similar to flexible member 640, 740 described above, may be inserted therethrough to provide support to malleable portion 830 as implant 800 is manipulated by the surgeon. FIG. 9C depicts a rear surface of panel 819 with receptacle 853 sized and shaped to receive key 850. Opening 854 is concentric with opening 851 and receives the same malleable flexible member as described above. In this manner, key 850 of an adjacent link 810 may be inserted within receptacle 853 and held in place by the malleable flexible member. Similar to flexible members 640, 740, above, the malleable flexible member inserted in implant 800 may include a hook along an exterior surface of either or both of an exterior surface of key 850 and/or receptacle 853 to maintain its position within implant 800.

Figure 10D:
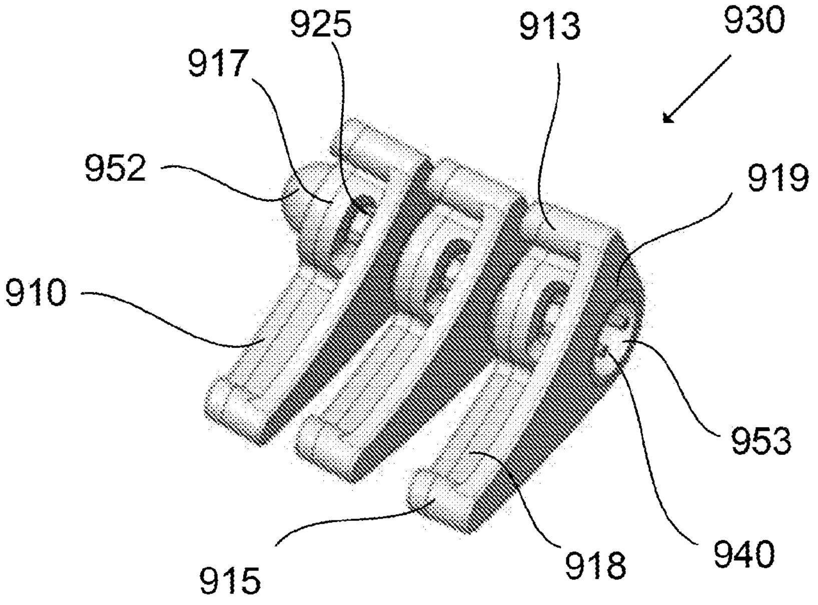
FIG. 10D is an isometric view of a malleable portion of the implant of FIG. 10A.

FIGS. 10A-10F illustrates an implant 900 according to another aspect of the disclosure. Implant 900 is similar to implants 10, 100, 200, 300, 400, 500, 600, 700, 800 detailed above with similar structures represented with reference numerals include a "9" preceding the previous reference numeral. Similar features will not be discussed in detail for reasons of brevity. In this aspect, as depicted in FIGS. 10A, implant 900 has a substantially triangular shape, and includes a malleable portion 930 and a stiff portion 931. Stiff portion 931 is shaped as if a number of links 910 have been fused together. As such, bone graft receiving portion 918*b*, ribs 932, and window 925*b* respectively share a similar shape to bone graft receiving portions 918*a*, panel 919, and window 925*a*. Stiff portion 931 provides additional support to implant 900 where malleability may not be as important during surgery. For instance, when implant 900 is placed along the spine, stiff portion 910 can be placed between transverse processes while malleable portions 930 are shaped to conform to their respective transverse processes. In alternative aspects, stiff portion 931 does not share a shape with links 910, and can be any shape (e.g., rectangular, triangular, or any other geometric or non-geometric shape) or length. Window 925*b* is an oblong slot along an exterior surface of housing 917. Although window 925*b* is adjacent an end of stiff portion 931, in alternative aspects, window 925*b* sit along any section of such portion. Moreover, in alternative aspects, there may be any number of windows 925 along the length of stiff portion 931. As depicted in FIGS. 10B-10C, stiff portion 931 has male end 912*b* including sphere 952*b*, and female end 914*b* including receptacle 953*b*, similar to ends 912*a*, 914*a*, as described below. In this manner, stiff portion 931 can key into adjacent links 910 such that adjacent malleable portions 930 can be manipulated around the ends of stiff portion 931. Stiff portion 931 has a passage 956*b* running through the length thereof.

Figure 10E:
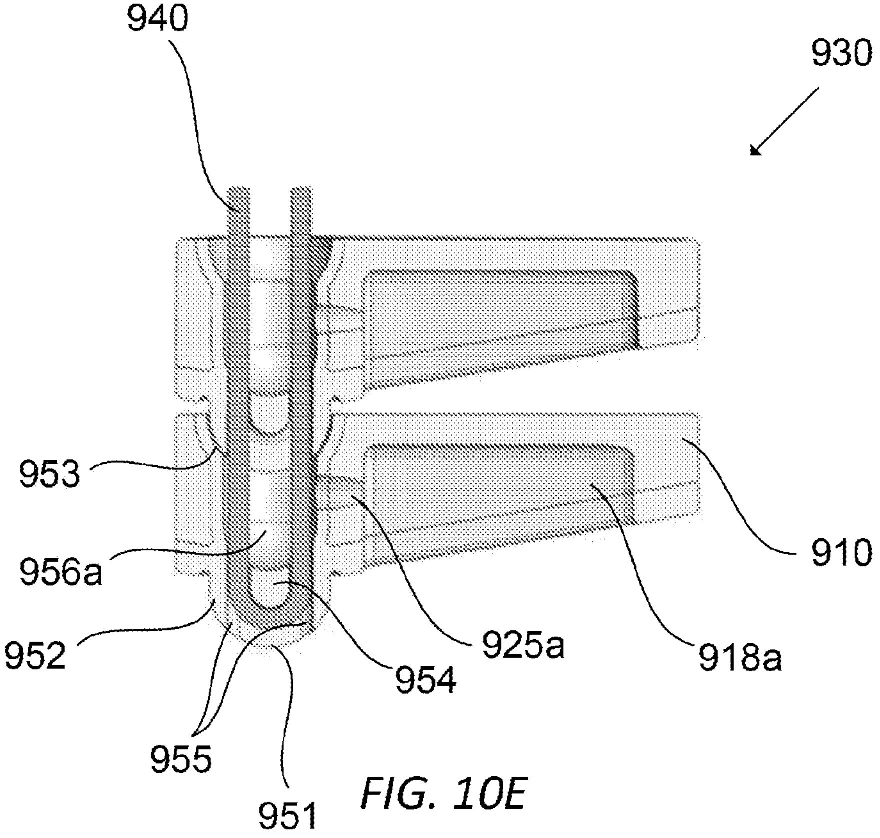
FIG. 10E is a cross-sectional view of the malleable portion of the implant of FIG. 10A.
Figure 10F:
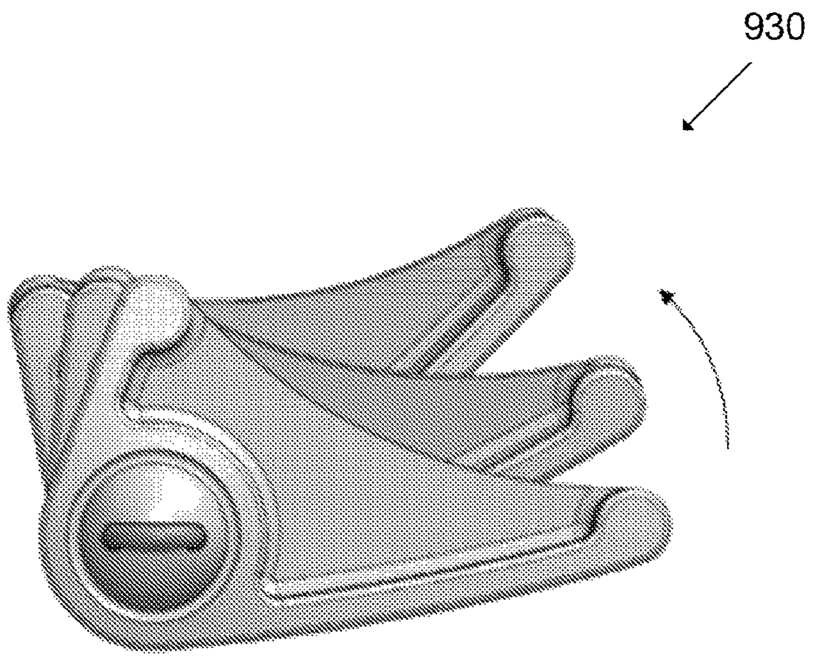
FIG. 10F is an end view of the implant of FIG. 10A.

As depicted in FIG. 10D-10E, malleable portions 930 include window 925*a* having a similar oblong shape as window 925*b*. A first opening of window 925*a* to passage 956*b* tapers to a second opening of window of 925*a* leading to bone graft receiving portion 918*a*. In alternative aspects, windows 925*a*, 925*b* may have any shape (e.g., rectangular, triangular, or any other geometric or non-geometric shape). Bone graft material may be placed along bone graft receiving portions 918*a*, 918*b* as well as being inserted within passages 956*a*, 956*b* through windows 925*a*, 925*b*. Receptacle 953*a* is shaped and sized to rotatably receive sphere 952*a*. Sphere 952*a* integrally extends from link 910 and includes opening 951 and channels 955 configured to receive free ends of flexible member 940. In this manner, a central portion of flexible member 940 contacts ledge 954 defined a distance within opening 951. The free ends of flexible member 940 extend through passage 956*a* and exit receptacle 953*a* to be inserted within an adjacent link 910, or to be tensioned and tied off in a knot (not shown) to secure implant 900. In alternative aspects, the free ends of flexible implant 940 may secure implant 900 through being twisted, clipped, stapled, melted, glued, or any other means of engaging each end of flexible implant 940 to keep links 910 together. FIG. 10F depicts malleable portion 930 rotated about a longitudinal axis defined by implant 900. An exemplary method of use will now be discussed with reference to implant 400. Once a working portal or area has been created on a patient, a surgeon may insert implant 400 within the patient alongside transverse processes of the spine similar to the methods described above for implants 10, 100, 200, 300. In a further aspect, implant 400 may be positioned adjacent the spinous process. Either before or after positioning implant 400, the surgeon may manipulate a section of malleable portion 430 to conform to a shape of adjacent structures, such as along a transverse process of the patient's spine, and/or a bone screw and spinal flexible member system. The surgeon manipulates the section of malleable portion 430 by bending or twisting a section of malleable portion 430. In this manner, the surgeon may position implant 400 at least partially within the space between each individual transverse or spinous process. Either before or after the surgeon manipulates the portion malleable portion 430, the surgeon may insert bone graft material within graft receiving portion 418 through windows 425, 426. In alternative aspects, with reference to implant 500, the surgeon may, in addition to the steps disclosed above, insert a fixation member, such as a bone screw (not shown), through hole 520 to anchor implant 500 to the patient. In further alternative aspects, a surgeon may secure implant 400, 500 through engaging attachment regions (not shown) with adjacent tissue, such as osseous tissue, in a similar manner to that described for attachment regions 16, 116*a*, 116*b*, 216, 316. In yet further alternative aspects, the surgeon may manipulate implant 400 to conform to adjacent implanted structures, such as a bone screw and spinal flexible member.

In a further alternative method, with reference to implant 600, the surgeon may desire to alter the length of malleable portion 630. In such a circumstance, the surgeon may, in addition to the steps disclosed above, disassemble malleable portion 630 by disengaging an end of flexible members 640 from being hooked along an exterior surface of ends 612 of implants 600. The surgeon can then pull or remove flexible members 640 from implant 600 and alter the length of malleable portion 630 by removing or adding links 610. For instance, where the surgeon decides to shorten implant 600, the surgeon may remove any number of links 610 until a desired length has been reached. Once the surgeon has removed a desired amount of links 610 the surgeon may reassemble malleable portion 630 by inserting a first male end of a first link 610 within a second female end of a second link 610. In an alternative aspect, the surgeon may add links 610 to increase the length of malleable portion 630. Flexible member 640 is then inserted within bone graft receiving portion 618 and the end of flexible member 640 hooked along the exterior surface of the end 612 of implant 600 to maintain links 610 positioned within each other. In alternative aspects, flexible member 640 may be unhooked and hooked along an exterior surface of end 614. The above disassembling/assembling steps may be performed before or during the surgery. Moreover, the surgeon may disassemble and reassemble malleable portion 630 more than once. For instance, the surgeon may check an altered implant 600 along a given measurement or along the spine to see if the altered implant 600 is at a desired length. The surgeon may then disassemble and reassemble malleable portion 630 until a desired length is met. Although the above method is in reference to implant 600, it should be understood that a method of use for implant 700 may also be performed with similar steps.

In an alternative method, with reference to implant 800, a similar method of use as described above may be used. In this aspect, the disassembling steps performed before or during the surgery may include a flexible member (not shown) being unhooked and removed from openings 851, 854 of links 810 before altering the length of malleable portion 830 through adding or removing links 810. To reassemble malleable portion 830, links 810 may be keyed within each other by inserting key 850 of a first link within a receptacle 853 of a second link 810. Openings 851, 854 may then be concentrically aligned so that the flexible member can be inserted through openings 851, 854. The flexible member can then be hooked in a manner similar to that described above. Moreover, in this method, malleable portion 830 is manipulated through rotating spheres 852 within their respective housing 817 of each link 810.

In an alternative method, with reference to implant 900, a similar method of use as described above may be used. In this aspect, the surgeon may additionally place stiff portion 931 between transverse processes and manipulate a section of malleable portions 930 to conform to the shape of the adjacent structures, such as an implanted structure or osseous tissue (e.g., transverse process or sacral bone). Before or during implant 900 is placed within the patient, bone graft material may be inserted into passage 956*a*, 956*b* through windows 925*a*, 925*b* as well as along bone graft receiving portions 918*a*, 918*b*. Additionally, where a surgeon decides to alter the length of malleable portions 930, the free ends of flexible implant 940 may be unsecured (e.g., through unknotting, cutting, or the like) and pulled from malleable portions 930 to alter the length of malleable portions 930, as described above. To assemble malleable portions 930, links 910 may be keyed in each other by inserting male ends 912*a* into female ends 914*a*. The free ends of flexible member 940 is then inserted within opening 951 and channels 954 of distant-most male end 912*a*. The free ends are inserted through channels 956*a*, 956*b* until the free ends exit the distant-most female end 914*a*. Flexible member 940 is then tensioned and secured by the surgeon (e.g., tied, twisted, clipped, stapled, melted, glued, or the like).

It is contemplated that the above implants can be formed through additive layer manufacturing, (ALM), i.e. 3D printing, such as powder based additive manufacturing, which uses a high energy beam, such as a laser beam or an electron beam. Such ALM processes preferably may be powder-bed based processes including selective laser sintering (SLS), selective laser melting (SLM), and electron beam melting (EBM), as disclosed in U.S. Pat. Nos. 7,537,664, 8,728,387, 9,135,374, 9,180,010, 9,456,901, 9,987,051, 10,028,841, and 10,271,958 U.S. Prov. Pat. App. No. 62/108,197, 62/196,371, 62/517,456 and 62/520,221, and U.S. Pat. App. Ser. No. 14/276,483, Ser. No. 14/969,695, Ser. No. 15/007,678, Ser. No. 15/007,348, Ser. No. 15/277,744, Ser. No. 15/982,704, and Ser. No. 16/039,701, the disclosures of each of which are hereby incorporated by reference herein, or other ALM processes such as binder jet additive manufacturing, stereolithography, multi-jet fusion, or powder-fed based processes including fused filament fabrication (FFF), e.g., fused deposition modeling (FDM). Moreover, the implants can be formed with any open design that allows for receiving and holding bone graft material while promoting in-growth and through-growth of osseous tissue. The implants can be formed with any material that is compatible with additive manufacturing and is biocompatible. The implants can further include a coating that also promotes biocompatibility, in- growth, and through growth.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method comprising:

positioning an implant having a first malleable portion adjacent a first transverse process, the first malleable portion including a plurality of links, wherein each link includes a non-symmetric cross-sectional shape, is uniform with an immediately adjacent link, and has a male end and a female end, the female ends being configured to receive the male ends and the male ends defining a sphere, and a flexible member extending therethrough; and manipulating a section of the first malleable portion to conform to a shape of the first transverse process.

2. The method of claim 1, further comprising inserting bone graft material into a bone graft receiving region defined within the implant.

3. The method of claim 2, wherein inserting bone graft material includes inserting the bone graft material through a first window defined along a length of the implant.

4. The method of claim 3, wherein the first malleable portion lies between the first window and a second window of the implant, the method further comprising inserting bone graft material through the second window into the bone graft receiving portion.

5. The method of claim 1, wherein manipulating the portion of the first malleable portion includes at least one of bending or rotating.

6. The method of claim 1, further comprising implanting a structure within a portion of the first transverse process.

7. The method of claim 6, where manipulating the portion of the first malleable portion includes conforming the first malleable portion to at least one of the first transverse process and the implanted structure.

8. The method of claim 1, further comprising inserting a fixation member through a hole adjacent an end of the implant.

9. The method of claim 1, further comprising inserting a first end of a first link of the plurality of links of the first malleable portion within a second end of a second link of the plurality of links of the first malleable portion.

10. The method of claim 9, further comprising inserting the flexible member through a portion of the implant.

11. The method of claim 10, wherein inserting the flexible member includes:

inserting the flexible member through a bone graft receiving portion of the implant; and hooking an end of the flexible member along an external surface of the implant.

12. The method of claim 10, wherein manipulating the section of the first malleable portion includes manipulating a section of the flexible member.

13. An implant comprising:

a first end and a second end separated from the first end by a first length extending along a longitudinal axis; and a first malleable portion between the first and second ends capable of moving a section of the medical implant transverse to the longitudinal axis, the first malleable portion including a plurality of links, wherein each link is substantially uniform with each other link and has a three-sided cross-sectional shape having one curved edge, a male end and a female end, the female ends being configured to receive the male ends, and a flexible member extending therethrough, wherein the male end defines a sphere.

14. A method comprising:

positioning an implant having a first malleable portion adjacent a first transverse process, the first malleable portion including a plurality of links, each link having a substantially triangular cross-section and defining a bone graft receiving region configured to receive bone graft material, a male end defining a sphere spaced apart from the bone graft receiving region, and a female end, the female ends being configured to receive the male ends; and manipulating a section of the first malleable portion to conform to a shape of the first transverse process.

15. The method of claim 14, wherein inserting the bone graft material includes inserting the bone graft material through a first window defined along a length of the implant.

16. The method of claim 14, wherein manipulating the portion of the first malleable portion includes at least one of bending or rotating.

17. The method of claim 14, further comprising implanting a structure within a portion of the first transverse process.

18. The method of claim 17, where manipulating the portion of the first malleable portion includes conforming the first malleable portion to at least one of the first transverse process and the implanted structure.

19. The method of claim 14, further comprising inserting a fixation member through a hole adjacent an end of the implant.

* * * * *